United States Patent [19]

Lang et al.

[11] 4,421,757

[45] * Dec. 20, 1983

[54] THIAZOLINE DERIVATIVES, PROCESSES FOR THEIR PREPARATION, THEIR USE AND PHARMACEUTICAL PREPARATIONS BASED ON THESE COMPOUNDS

[75] Inventors: Hans-Jochen Lang, Hofheim an Taunus; Bernhard Seuring, Frankfurt am Main; Ernold Granzer, Kelkheim, all of Fed. Rep. of Germany

[73] Assignee: Hoechst Aktiengesellschaft, Frankfurt am Main, Fed. Rep. of Germany

[*] Notice: The portion of the term of this patent subsequent to Aug. 24, 1999 has been disclaimed.

[21] Appl. No.: 335,149

[22] Filed: Dec. 28, 1981

[30] Foreign Application Priority Data

Dec. 30, 1980 [DE] Fed. Rep. of Germany ....... 3049460

[51] Int. Cl.³ .................. C07D 277/38; A61K 31/425
[52] U.S. Cl. .................................... 424/270; 548/197; 546/209; 424/267
[58] Field of Search ................ 548/197; 424/270, 267; 546/209

[56] References Cited

U.S. PATENT DOCUMENTS

| 4,061,647 | 12/1977 | Lang et al. | 548/197 |
| 4,061,761 | 12/1977 | Lang et al. | 548/197 |
| 4,083,979 | 4/1978 | Lang et al. | 548/197 |
| 4,118,501 | 10/1978 | Lang et al. | 548/197 |
| 4,346,088 | 8/1982 | Lang et al. | 548/197 |

FOREIGN PATENT DOCUMENTS

| 2533821 | 2/1977 | Fed. Rep. of Germany | 548/197 |
| 2546165 | 4/1977 | Fed. Rep. of Germany | 548/197 |
| 2926771 | 1/1981 | Fed. Rep. of Germany | 548/197 |

Primary Examiner—Robert Gerstu
Attorney, Agent, or Firm—Curtis, Morris & Safford

[57] ABSTRACT

Thiazoline derivatives of the formula I

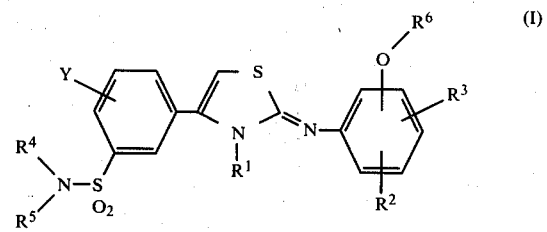

wherein $R^1$ to $R^6$ and Y have the meanings given, their physiologically tolerated salts, processes for their preparation, pharmaceutical preparations based on these compounds as well as their use as medicaments comprise the invention. In addition, intermediates are described.

9 Claims, No Drawings

THIAZOLINE DERIVATIVES, PROCESSES FOR THEIR PREPARATION, THEIR USE AND PHARMACEUTICAL PREPARATIONS BASED ON THESE COMPOUNDS

The invention relates to compounds of the general formula I

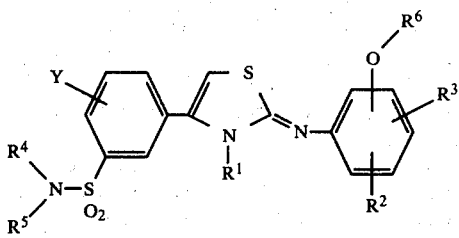

which, as such or in the form of their pharmacologically tolerated salts, possess valuable pharmacological properties, and therefore are suitable as medicaments.

In the formula, $R^1$ is alkyl with 1 to 3 C atoms, $R^2$ and $R^3$ are hydrogen, halogen, alkyl or alkoxy with in each case 1 to 4 C atoms, and are identical or different, $R^4$ and $R^5$ are hydrogen or alkyl with 1 to 4 C atoms, and are identical or different, or together with the N atom form a saturated ring with up to 6 ring members, $R^6$ is hydrogen or acyl with 1 to 4 C atoms and Y is hydrogen, halogen or methyl.

The invention further relates to a process for the preparation of the compounds of the general formula I, which comprises, (a) reacting, under condensation conditions, compounds of the general formula II

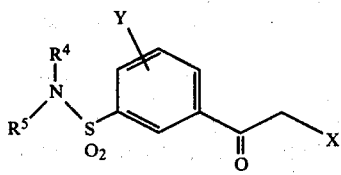

wherein $R^4$, $R^5$ and Y have the abovementioned meaning and X is a leaving-group such as halogen, $CH_3SO_2$—O— or

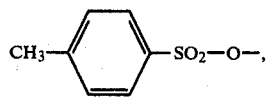

with a thiourea of the general formula III

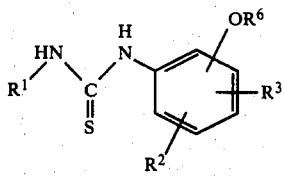

wherein $R^1$, $R^2$, $R^3$ and $R^6$ have the abovementioned meaning or (b) eliminating water from compounds of the formula IV

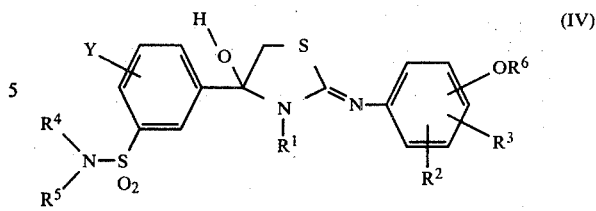

wherein $R^1$ to $R^6$ and Y have the abovementioned meaning, or (c) reacting compounds of the general formula V

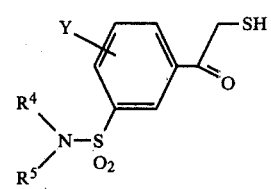

with compounds of the general formula VI

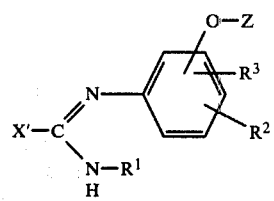

wherein $R^1$ to $R^5$ have the abovementioned meaning, Z is a protective group for the phenolic hydroxyl group, such as, for example, an acyl group with 1 to 4 C atoms, methyl or tert.-butyl, and X' is a leaving-group, such as, for example, halogen, methoxy or methylthio, or (d) converting, by hydrolytic or solvolytic cleavage, compounds of the general formula VII

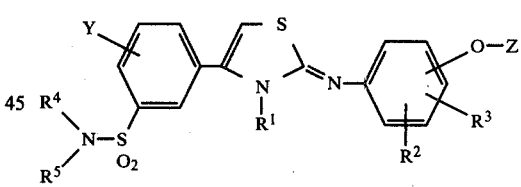

wherein $R^1$ to $R^5$ and Y have the meanings mentioned for formula I, and Z has the meaning mentioned for formula VI, into the compounds of the formula I, wherein $R^6$ is hydrogen, or (e) converting compounds of the general formula I, wherein $R^1$ to $R^5$ and Y have the abovementioned meaning, and $R^6$ is hydrogen, by means of an acylating agent, such as an acyl chloride or acyl anhydride, into compounds of the formula I with $R^6$ having the meaning of acyl with 1 to 4 C atoms, and, if appropriate, converting one of the compounds of the general formula I, obtained by one of the routes (a) to (e), into its acid addition salt by means of organic or inorganic acids of the general formula H-A, or converting the resulting salts of the compounds of the general formula I, by means of bases into the free basic compounds of the formula I, or converting a resulting compound of the formula I, wherein $R^6$ is hydrogen, by means of organic or inorganic bases into phenolate salts, or converting correspondingly obtained salts by means of acids into the free basic compounds of the formula I.

Examples of inorganic acids H–A are hydrogen halide acids such as hydrochloric acid and hydrobromic acid, as well as sulfuric acid, phosphoric acid, and amidosulfonic acid.

Examples which may be mentioned of organic acids H–A are methanesulfonic acid and p-toluenesulfonic acid.

Examples of inorganic bases for the formation of phenolate salts are sodium hydroxide solution (NaOH) or potassium hydroxide solution (KOH), and examples of organic bases are sodium methylate, sodium ethylate, potassium tert.-butylate or tetraethylammonium hydroxide.

The compounds of the formula IV are new. Thus the invention also relates to compounds of the formula IV

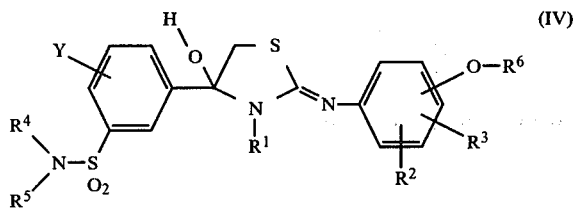

wherein $R^1$ to $R^6$ and Y have the meanings given for formula I, or to their acid addition salts and phenolate salts. They are suitable as precursors for the preparation of compounds of the general formula I.

The compounds of the formula I according to the invention can also exist in their possible isomeric structures, but for purposes of simplification only one of the possible isomeric forms of each individual substance will be given.

The procedure denoted (a) is preferably performed by reacting the compounds Ii with the thioureas III in the molar ratio 1:1 to 1:1.5. In general, no significant advantages are obtained with larger molar excesses of thiourea.

The reaction is advantageously performed in inert polar organic solvents such as dimethylformamide, dimethylacetamide, ethylene glycol ethers, acetone or tetrahydrofuran, particularly advantageously in highly polar protic solvents such as methanol, ethanol, isopropanol, n-butanol, acetic acid, propionic acid, formic acid as well as in mixtures of water and the solvents mentioned, and anhydrous mixtures of the solvents mentioned are also suitable. Equally, the reaction can also be performed without use of a solvent by warming the reaction mixture to a temperature range between 80° and 220° C., preferably between 100° and 180° C. When a solvent is used, the preferred temperature range is 50° to 150° C.

The reaction time is largely dependent on the solvent and the reaction temperature used, and in general lies between 15 minutes and 24 hours. The quantitative course of the reaction to give the compounds I according to the invention is advantageously followed by thin layer chromatography on silica gel plates.

In many cases, the compounds I according to the invention separate out in the course of the reaction as sparingly soluble, filterable acid addition salts; if this does not occur, the solvent is evaporated, and, if appropriate, the yield can be increased by subsequent addition of a suitable precipitant, such as, for example, ethyl acetate, diethyl ether, diisopropyl ether, acetone or acetonitrile.

The thioureas III used are prepared by a known method by reaction of amines with isothiocyanates, carbon disulfide or thiophosgene (c.f. Houben-Weyl, "Methoden der organischen Chemie" (Methods of Organic Chemistry), Volume 9, page 384, 4th edition, Georg-Thieme-Verlag, Stuttgart, 1955).

The compounds of the general formula II can be obtained by several literature methods (c.f. for example German Offenlegungsschrift No. 2,436,263).

According to the procedure denoted (b), 2-arylimino-4-hydroxy-4-(3-sulfamoylphenyl)-thiazolidines (IV) are thermally dehydrated, preferably by proton catalysis, to give the compounds of the general formula I according to the invention. This is performed advantageously in polar organic solvents, suitable protic solvets being, for example, methanol, ethanol, propanol, isopropanol, 1-butanol or 2-butanol, ethylene glycol monomethyl ether, diethylene glycol monomethyl ether or lower aliphatic carboxylic acids, such as acetic acid, propionic acid, formic acid or also mixtures of the solvents mentioned with one another or with water.

Inorganic or organic protonic acids can be used as catalysts, in particular one of the aliphatic carboxylic acids mentioned as a solvent. The dehydration of the compounds IV can, in principle, also be performed without use of either a catalyst or a solvent.

The reaction can be performed in a temperature range between 0° and 200° C., lower temperatures leading to long reaction times, and higher temperatures increasing the danger of the formation of by-products. The preferred temperature range is between 50° and 150° C., the reaction particularly advantageously being performed in boiling methanol, ethanol, propanol, acetone or acetic acid.

The reaction mixture is advantageously worked up analogously to the method given in procedure (a).

The compounds of the general formula IV are obtained by methods known in themselves, for example analogously to the procedures given in German Offenlegungsschrift No. 2,436,263. If the preparation of compounds of the formula IV of the highest possible purity is desired, the mildest possible reaction conditions and temperatures and work-up conditions under 40° C. should be chosen.

According to procedure (c), compounds of the general formula V are brought to reaction with compounds of the formula VI advantageously in a polar organic solvent, for example in lower alcohols with 1 to 4 C atoms, ethylene glycol monomethyl ether and ethylene glycol dimethyl ether, diethylene glycol monomethyl ether or diethylene glycol dimethyl ether, acetone, tetrahydrofuran, ethyl acetate, or dimethylformamide.

The reaction is advantageously performed between 0° and 80° C., preferably between 15° and 40° C., and, after the exothermic reaction has subsided, the mixture is heated to temperatures between 60° and 140° C. until completion of the formation of the compounds of the formula I. The course of reaction is preferably followed by thin layer chromatography on silica gel plates. The reaction time lies between 5 and 60 hours. Compounds VI and above all, compounds V, in which $R^4$ and $R^5$ are organic radicals with the abovementioned meaning, are particularly suitable for this reaction.

The compounds of the formula V used in procedure (c) can be prepared by methods known in the literature (e.g. German Offenlegungsschrift No. 2,436,263). The preparation of compounds of the general formula VI is also described in the literature (e.g. Chem. Ber. 97, 1232 (1964).

The procedure (d) involves subjecting compounds of the general formula VII, wherein Z is an acyl radical, to solvolysis by a method which is known in itself, in which the compounds VII are treated at temperatures between 20° and 100° C., preferably between 30° and 60° C., with the solution of an inorganic hydroxide M-OH, where M has the meaning of e.g. Li, Na, K or ammonia, or with the solution of an organic primary or secondary amine, such as methylamine, dimethylamine, ethylenediamine or morpholine, in water, methanol, ethanol, isopropanol, in dioxane, tetrahydrofuran, chloroform, ethylene glycol monomethyl ether or ethylene glycol dimethyl ether, or in mixtures of the solvents mentioned, it being advisable to perform the reaction under an inert gas, such as nitrogen or argon. In working up the reaction mixture, it is preferable to remove solvent in vacuo under reduced pressure, to take up the residue in water, to bring the pH to 4-6 with an acid such as acetic acid or hydrochloric acid, warming to between 40° and 80°, and to filter off the precipitate.

If Z has the meaning of an alkyl radical, the ether derivatives of the general formula VII are preferably cleaved in an acid medium.

The use of the tert.-butyl ethers (with Z=tert.-butyl) is particularly advantageous, since they are readily cleaved in inorganic or organic acids, e.g. in trifluoroacetic acid or in boron trifluoride-containing acetic acid, or in methanolic hydrochloric acid at temperatures between 20° and 80° C. The course of the reaction is advantageously followed by thin layer chromatography. To work up the reaction mixture, the solvent is removed under reduced pressure, after adding water the residue is brought to pH 5 to 6, preferably with a weak base, such as, for example, ammonium acetate, and the precipitate is filtered off.

It is advantageous to remember that, in the alkaline cleavage of the radical —OZ, one mole of base is necessary, and in the case where $R^4$ and/or $R^5$ are hydrogen, it is preferable to use either one or two further moles of basic reagent.

In the performance of the procedure (e), compounds of the formula I, wherein $R^6$ is hydrogen, are brought to reaction, in a method which is known in itself, with an acylating agent such as ketene, but preferably with an acyl anhydride or acyl chloride, the conditions of the Schotten-Baumann reaction having been found particularly suitable (Ulmanns Encyklopädie der technischen Chemie (Encyclopedia of Technical Chemistry), 3rd Volume, page 88, Verlag Urban und Schwarzenberg, Munich-Berlin (1953), Houben-Weyl, Methoden der Organischen Chemie (Methods of Organic Chemistry), Georg-Thieme Verlag, Stuttgart, 1952, Volume 8, page 545, 655; N.O.V. Sonntag, Chem. Rev, 52, 272 (1953)). Preferred auxiliary bases are pyridine, triethylamine or sodium hydroxide solution, the reaction being advantageously performed in a temperature range of 20° to 140° C.

The compounds of the formula I can be reversibly reacted with an acid of the formula H-A in a suitable solvent. The compounds I can be added to the pure acids, preferably at temperatures between 0° and 60° C., insofar as these acids are liquid or have a melting point not substantially higher than 60° C., and insofar as they do not bring about side reactions. It is advantageous to use a solvent, such as, for example, water, dioxane, tetrahydrofuran, ether, a lower alkyl ester of acetic acid with 1 to 4 C atoms in the alkyl radical, acetonitrile, acetone, methyl ethyl ketone etc., and lower alcohols with 1 to 4 C atoms and carboxylic acids with 2 to 4 C atoms have been found paticularly suitable. 1–1.5 moles of the acids H-A are used per mole of the compounds I, but larger amounts of acid can also be used. It is advantageous to operate at temperatures between 0° and 120° C., preferably between 10° and 60° C.

The salts according to the invention are advantageously isolated, after reaction in aqueous medium, when a solution is obtained, by evaporation of the water under mild conditions, preferably by freeze-drying. Operating in organic solvents, the sparingly soluble acid addition salts frequently separate out after addition of the corresponding acid H-A. If a solution is obtained, the acid addition compounds are precipitated, if appropriate after previous concentration, with a suitable precipitant. Suitable precipitants are the solvents described in procedure (a) for the same purpose.

The acid addition products, even when very highly purified, are very often obtained in the form of viscous oils or amorphous glass-like products. These amorphous products can frequently be brought to crystallization, if appropriate by warming to 40° to 80° C., by treatment with an organic solvent.

The acid addition products can be deprotonated in a suitable solvent by treatment with bases, in particular with triethylamine or sodium hydrogen carbonate solution to produce the compounds of the general formula I. Working in an aqueous medium, the sparingly-soluble free basic compounds I precipitate out and can be separated and isolated by filtration or extraction with an organic solvent, preferably with ethyl acetate. Lower alcohols with 1 to 4 C atoms, preferably methanol and ethanol are particularly suitable as organic reaction media. The reaction to the compounds I occurs spontaneously. The reaction is performed between −35° and 100° C., preferably between 0° and 60° C. If a water-miscible organic solvent is used, the free bases of the formula I are precipitated, if necessary after previous concentration, by addition of water. If a water-immiscible solvent is used, the reaction mixture is washed, after the reaction, advantageously with water and the organic solvent evaporated, if necessary after previous drying.

Allowing at least 1 mole of a sufficiently strong base to react with compounds of the formula I, wherein at least one of the substituents $R^4$, $R^5$ or $R^6$ is hydrogen, produces, by deprotonation of the sulfonamide group or of the phenolic OH group, salts of the general formula Ib

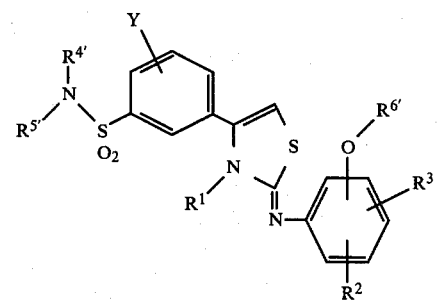

wherein at least one of the substituents $R^{4'}$, $R^{5'}$ or $R^{6'}$ is the cation of an alkali metal or an alkaline earth metal, and the other substituents $R^{4'}$, $R^{5'}$ or $R^{6'}$ respectively have the meanings given for $R^4$, $R^5$ and $R^6$.

Bases which may be used are hydroxides of the alkali and alkaline earth metals, preferably NaOH and KOH, alkali and alkaline earth alcoholates, $NaOCH_3$ and $NaOC_2H_5$, NaH, sodium methylsulfinylmethide etc.

Solvents which may be used are water or polar organic solvents such as methanol, ethanol, isopropanol, n-butanol, dimethylformamide, dimethylsulfoxide, diethylene glycol dimethyl ether and acetonitrile.

The compounds I according to the invention are re-formed by addition of equivalent amounts of a suitable acid H-A.

This reversible acid-base reaction can be employed to purify the compounds I.

The preferred compounds according to the invention are those of the general formula I, in which the substituents have the meanings listed in Table 1 which follows:

TABLE 1

$R^1$ = methyl or ethyl
$R^2$ = hydrogen or chlorine
$R^3$ = hydrogen, chlorine or methyl
$R^4$ = hydrogen, methyl or ethyl
$R^5$ = hydrogen or methyl
$R^6$ = hydrogen, $-COCH_3$ or $-COC_2H_5$
Y = bromine, chlorine or methyl in the 4-, 5- or 6-position to the thiazoline ring, the sulfamoyl radical being fixed in the 3-position;

among these, the particularly preferred compounds are those compounds of the formula I, in which the substituents have the meanings given in Table 2:

TABLE 2

$R^1$ = methyl
$R^2$, $R^3$ = hydrogen
$R^4$, $R^5$ = hydrogen and/or methyl
$R^6$ = hydrogen, the OH group being in the 4-position to the imino group
Y = chlorine in the 4-position to the thiazoline ring Apart from the thiazoline derivatives given in the practical examples and in the Tables 4 and 5, the compounds of the general formula Ia and IVa, or their acid addition products, collated in the following Table 3 can also be obtained according to the invention:

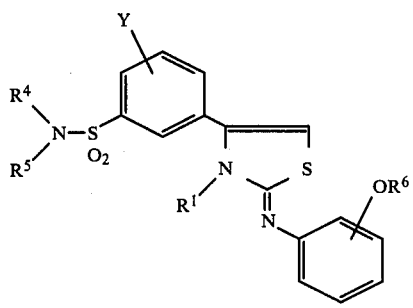
(Ia)

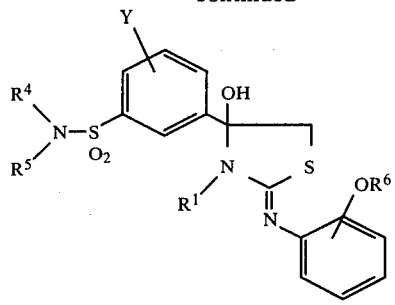
(IVa)

TABLE 3

(Meaning of the symbols: Me = methyl, Et = ethyl, n-Pr = n-propyl, i-Pr = isopropyl, Bu = butyl, t-Bu = tert.-butyl, Ac = acetyl, Prop = propionyl, Ph = phenyl; the numbers given before the substituent indicate its position on the appropriate phenyl ring, the thiazoline ring being fixed in the 1-position and the sulfamoyl radical being fixed in the 3-position.)

| Serial No. | Y | $R^1$ | $R^4$ | $R^5$ | $OR^6$ |
|---|---|---|---|---|---|
| 1 | 5-Cl | Me | H | H | 4-OH |
| 2 | 5-Cl | Me | H | H | 3-OH |
| 3 | 5-Cl | Me | H | H | 2-OH |
| 4 | 5-Cl | Me | H | Me | 4-OH |
| 5 | 5-Cl | Me | H | Me | 3-OH |
| 6 | 5-Cl | Me | H | Me | 3-OH |
| 7 | 5-Cl | Me | Me | Me | 3-OH |
| 8 | 6-Cl | Me | H | H | 4-OH |
| 9 | 6-Cl | Me | H | H | 3-OH |
| 10 | 6-Cl | Me | H | H | 2-OH |
| 11 | 6-Cl | Me | H | Me | 4-OH |
| 12 | 6-Cl | Me | H | Me | 3-OH |
| 13 | 6-Cl | Me | H | Me | 2-OH |
| 14 | 6-Cl | Me | Me | Me | 3-OH |
| 15 | 6-Cl | Me | Me | Me | 4-OAc |
| 16 | 6-Cl | Me | Me | Me | 2-OAc |
| 17 | 6-Cl | Me | Me | Me | 3-OAc |
| 18 | 6-Cl | Me | Me | Me | 4-OProp |
| 19 | 5-Cl | Me | Me | Me | 4-OAc |
| 20 | 5-Cl | Me | Me | Me | 3-OAc |
| 21 | 4-Me | Me | H | H | 4-OH |
| 22 | 4-Me | Me | H | Me | 4-OH |
| 23 | 4-Me | Me | Me | Me | 3-OH |
| 24 | 4-Me | Me | Me | Me | 2-OH |
| 25 | 5-Me | Me | H | H | 4-OH |
| 26 | 5-Me | Me | Me | Me | 3-OH |
| 27 | 5-Me | Me | Me | Me | 2-OH |
| 28 | H | Me | H | H | 4-OH |
| 29 | H | Me | Me | Me | 4-OH |
| 30 | H | Me | H | Me | 4-OH |
| 31 | H | Me | H | H | 2-OH |
| 32 | H | Me | Me | Me | 3-OH |
| 33 | H | Me | Me | Me | 3-OH |
| 34 | H | Me | H | H | 3-OH |

The compounds of the formula I according to the invention are valuable medicaments and are distinguished by a very favorable effect on the serum lipoproteins. Thus they can be used as medicaments, particularly for influencing the serum lipoproteins. The invention thus relates also to pharmaceutical preparations based on the compounds of the formula I, and their pharmacologically tolerated salts as well as the use as medicaments.

4-Phenyl-2,3-dihydrothiazoline derivatives have been reported in the literature to possess anorectic, CNS-stimulating and diuretic activity, these compounds having no sulfonamide substitution in the phenyl part, and the 2-imino function not being substituted by aryl (c.f. U.S. Pat. No. 3,671,533, German Offenlegungsschrift No. 1,938,674). 3-Alkyl-4-phenyl-2-phenylimino-4- thiazolines (c.f. Univ. Kansas Sci. Bull. 24, 45–49 (1936)) have also been described, in which the phenyl radical in the 4-position has no sulfonamide group. Variously substituted 4-(3-sulfamoyl-phenyl)-3-alkyl-2-imino-4-thiazolines or -thiazolidines are also mentioned in the literature, and particularly as diuretics (c.f. "Diuretic Agents", E. J. Cragoe, Jr., Editor; ACS-Symposium Series 83, page 24, Washington D.C., (1978)).

Thus it was surprising that the compounds of the formula I according to the invention show a very strong and favorable influence on the serum lipoproteins, whilst the thiazoline derivatives mentioned in the literature above cause no effects or only slight effects clearly inferior in respect of quality and quantity.

It is generally recognized, that hyperlipoproteinemias represent an important risk factor for the development of arteriosclerotic vascular changes, in particular of coronary heart disease For the prophylaxis and the regression of atherosclerotic changes, the reduction of raised serum lipoproteins has thus an extreme importance. However, this depends on very particular classes of serum lipoproteins, since the low density (LDL) and very low density lipoproteins (VLDL) represent an atherogenic risk factor, whilst the high density lipoproteins (HDL) represent a protection against coronary heart disease. Hypolipidemic agents should thus lower the VLDL cholesterol and LDL cholesterol in the serum, while, if possible, having no influence on the concentration of HDL cholesterol or even increasing it. The compounds according to the invention have valuable therapeutic properties. Thus they lower primarily the concentration of LDL and VLDL, whilst the HDL fraction is either decreased to a substantially smaller extent, or is even increased. They have, therefore, application for the prophylaxis and regression of atherosclerotic changes, since they eliminate a causative risk factor. These include not only the primary hyperlipoproteinemias, but also certain secondary hyperlipidemias such as, arise e.g. in diabetes. The relative liver-weight is not substantially altered by the compounds I, while clofibrate, which is used as a hypolipidemic standard, leads to a great increase in the relative liver-weight.

The effect e.g. of the compounds listed in the following Table I on the serum liproproteins, was investigated on male Wistar rats, which were treated for 7 days by gavage with the compounds according to the invention suspended in polyethylene glycol 400. In addition, a control group which received only the solvent polyethylene glycol 400, and a group of rats, which for comparison received the standard hypolipidemic agent clofibrate dissolved in polyethylene glycol 400, were set up. As a rule, 10 animals were used in each group, from which, at the end of the treatment, blood was taken from the orbital plexus under light ether anesthetic. The serum obtained from this was pooled. The serum lipoproteins were separated in the ultracentrifuge in the following ranges of density: VLDL 1.006; LDL 1.006 to 1.04; HDL 1.04 to 1.21.

The cholesterol, contained in the lipoprotein fractions isolated by ultracentrifugation, was determined completely enzymatically by the CHOD-PAP method using the test combination from Boehringer-Mannheim, and the values were converted into g/ml serum. The change of the lipoprotein-cholesterol in the treated group compared with a control group under the same conditions was determined. It was observed that clofibrate brings about a roughly equal depression of the LDL fraction and HDL fraction, while the new compounds exert a highly selectively depressing effect on the atherogenic lipoprotein fractions (VLDL and LDL), and leave the protective HDL fraction essentially uninfluenced or even increase it.

TABLE I

Alteration of the serum lipoprotein level in rats after 7 days peroral administration of the compounds

| Compound according to example | Dose mg/kg/ day | Changes in cholesterol (in comparison to the control group) | | | |
|---|---|---|---|---|---|
| | | in Serum | in the serum lipoprotein fraction | | |
| | | | VLDL | LDL | HDL |
| 2 | 10 | −9 | −54 | −17 | −4 |
| 5 | 10 | +2 | −24 | −20 | +7 |
| 14 | 10 | −12 | −43 | −27 | −8 |
| 8 | 30 | −9 | −55 | −52 | +19 |
| 32 | 10 | −21 | −21 | −32 | −6 |
| 42 | 10 | −25 | −68 | −44 | −4 |

Possible therapeutic preparations of the compounds of the formula I are primarily tablets, coated tablets, capsules, suppositories and syrups. The new compounds can be used either alone or mixed with pharmacologically acceptable carriers. An oral administration form is preferred. For this purpose, the active compounds are preferably mixed with substances which are known in themselves, and converted, by methods which are known in themselves, into appropriate forms of administration, such as tablets, hard capsules, aqueous or oily suspensions or aqueous or oily solutions. Examples of inert carriers which can be used are magnesium carbonate, lactose or corn starch with addition of other substances e.g. magnesium stearate. The preparation can be in the form of dry or moist granulate. Suitable oily carriers or solvents are particularly plant and animal oils such as e.g. sunflower oil or cod-liver oil. A suitable daily dose is about 50 mg to 5 g, preferably 100 to 1000 mg. A dosage unit contains preferably 50 to 1000 mg, in particular 250 to 500 mg.

For the treatment of disorders of the lipid metabolism, the preparations can contain, apart from the usual fillers and carriers, an additional active ingredient such as e.g. an antihypertensive agent, for example a saluretic, reserpine, hydralazine, guanethidine, α-methyldopa, clonidine or a β-sympathicolytic agent, or an antihyperuricemic agent, an oral antidiabetic agent, a geriatric agent or a compound which acts to increase the blood supply.

The pure precursors of the general formula IV according to the invention show, in comparison to the compounds of the formula I according to the invention, either no effect or clearly weaker effects on the serum lipoproteins; however, they possess, as do the structurally related thiazolidine derivatives (c.f. German Offenlegungsschrift No. 2,436,263) in some cases a very good salidiuretic activity.

In the following examples, the quoted melting points and decomposition points are not corrected.

EXAMPLE 1

4-(4-Chloro-3-dimethylsulfamoylphenyl)-2-(4-hydroxyphenylimino)-3-methyl-4-thiazoline hydrobromide (a) 6.8 g (0.02 mole) of 2-bromo-4'-chloro-3'-dimethylsulfamoylacetophenone and 3.7 g (0.021 mole) of 1-(4-hydroxyphenyl)-3-methylthiourea in 100 ml of ethanol are heated in the course of 1 hour to boiling. 50 ml of glacial acetic acid are now added and heating at the boiling point is continued for 2-3 hours. After distilling off the solvent in a water-pump vacuum, the residue is treated with diisopropyl ether, ethyl acetate or diethyl ether and filtered. Colorless crystals, m.p. 276°-281° C. (decomp.).

(b) 5.23 g (0.01 mole) of 4-(4-chloro-3-dimethylsulfamoylphenyl)-3-methyl-2-(4-hydroxyphenylimino)-thiazolidin-4-ol hydrobromide in 70 ml of glacial acetic acid are heated in the course of 20 min. to boiling. After cooling, the crystallization is completed by addition of about 150 ml of diisopropyl ether, the mixture is stirred for a further hour at room temperature and filtered. Colorless crystals, m.p. 275°-279° C. (decomp.).

EXAMPLE 2

4-(4-Chloro-3-dimethylsulfamoylphenyl)-2-(4-hydroxyphenylimino)-3-methyl-4-thiazoline (a) 4.24 g (0.01 mole) of 4-(4-chloro-3-dimethylsulfamoylphenyl)-2-(4-hydroxyphenylimino)-3-methyl-4-thiazoline hydrobromide are suspended in 120 ml of methanol and the reaction mixture, after addition of 4 g (0.04 mole) of triethylamine, is stirred at room temperature for 45 min. After distilling off the solvent under reduced pressure, the residue is brought to crystallization by treatment with water. Colorless to pale yellow crystals, m.p. 188°-192° C. (from ethanol).

(b) 4.4 g (0.01 mole) of 4-(4-chloro-3-dimethylsulfamoylphenyl)-2-(4-hydroxyphenylimino)-3-methyl-thiazolidin-4-ol in 60 ml of glacial acetic acid are heated to boiling for 1 hour, the solvent is distilled off and the residue is brought to crystallization by addition of water. M.p. 189°-191° C.

(c) A mixture of 2.9 g (10 mmoles) of 4'-chloro-3'-dimethylsulfamoyl-acetophenone-2-thiol (c.f. German Offenlegungsschrift No. 2,436,263) and 2.2 g (10 mmoles) of N-methyl-N'-(4-hydroxyphenyl)-chloroformamidine hydrochloride (m.p. 205°-206° C. (decomp.), prepared from 1-methyl-3-(4-hydroxyphenyl)-thiourea and phosgene in tetrahydrofuran) in about 50 ml of anhydrous isopropanol, at 10° to 15° C., with exclusion of moisture, is treated dropwise in the course of 30 min. with a solution of 2 g of triethylamine in a little isopropanol. After addition of about 50 ml of chloroform, the mixture is stirred overnight at room temperature, 20 ml of glacial acetic acid are added and the mixture is heated for 1 hour under reflux. After removing the solvent in vacuo, the residue is taken up in about 50 ml of chloroform, washed several times with a little water and, after drying and evaporating the organic phase, it is subjected to column chromatography (silica gel; eluting agent toluene/ethyl acetate 1:10 to 1:1). The product fractions are evaporated and a beige-colored powder is obtained which gives, after recrystallization from ethyl acetate/ethanol, colorless crystals of m.p. 190°-192° C.

(d) A suspension of 1.7 g of 4-(4-chloro-3-dimethylsulfamoylphenyl)-2-(4-acetoxyphenylimino)-3-methyl-4-thiazoline (Example 8) in 30 ml of ethanol and 20 ml of water is brought to pH 11-12 with 2 N caustic soda and stirred at room temperature for 3 hours. After neutralization with 2 N hydrochloric acid, and repeated extraction with methyl acetate, the organic phases are dried, evaporated and the residue recrystallized from ethyl acetate/ethanol. Beige-colored crystals of m.p. 188°-190° C., identical with the product obtained by the method (a)-(c) by thin layer comparison.

EXAMPLE 3

4-(4-Chloro-3-methylsulfamoylphenyl)-2-(4-hydroxyphenylimino)-3-methyl-4-thiazoline hydrochloride (a) Analogously to the procedure given in Example 1 (a), by reaction of 2,4'-dichloro-3'-methylsulfamoylacetophenone and 1-(4-hydroxyphenyl)-3-methylthiourea. Colorless crystals, m.p. 302° C. (decomp.).

(b) 4.1 g of 4-(4-chloro-3-methylsulfamoylphenyl)-2-(4-hydroxyphenylimino)-3-methyl-4-thiazoline are suspended in 150 ml of methanol and made acid with saturated ethereal hydrogen chloride solution, the solvent is distilled off and the residue is recrystallized from ethanol. M.p. 300°-302° C. (decomp.).

EXAMPLE 4

4-(4-Chloro-3-dimethylsulfamoylphenyl)-2-(4-hydroxyphenylimino)-3-methyl-4-thiazoline hydrochloride is obtained analogously to the procedure given in Example 3(a) and (b). Colorless crystals, m.p. 264° C. (decomp.).

EXAMPLE 5

4-(4-Chloro-3-sulfamoylphenyl)-2-(4-hydroxyphenylimino)-3-methyl-4-thiazoline

From 6.2 g (20 mmoles) of 2-bromo-4'-chloro-3'-sulfamoylacetophenone and 3.7 g (21 mmoles) of 1-(4-hydroxyphenyl)-3-methylthiourea in 80 ml of acetone by stirring at room temperature for one hour and subsequent stirring under reflux for 1 hour after addition of 100 ml of glacial acetic acid. The hydrobromide of the title compound (m.p. 274° C. with decomp.) is obtained by evaporation of the reaction mixture and is converted into the product by stirring with 100 ml of saturated aqueous sodium bicarbonate solution, washing with water and recrystallizing from ethanol/water. M.p. 224°-226° C.

EXAMPLE 6

4-(3-Dimethylsulfamoyl-5-methylphenyl)-2-(4-hydroxyphenylimino)-3-methyl-4-thiazoline 5.9 g (12 mmoles) of 4-(3-dimethylsulfamoyl-5-methylphenyl)-2-(4-hydroxyphenylimino)-3-methyl-4-thiazoline hydrobromide are suspended in about 50 ml of methanol and treated with 5 ml of triethylamine. After stirring the resulting red solution for about 30 min. at room temperature, a light-colored solid precipitates. This is stirred for a short while longer, filtered off and recrystallized from isopropanol. Colorless crystals, m.p. 218°-220° C.

The starting material is mentioned in Example 83 and was prepared analogously to Example 1a. The 2-bromo-5'-methyl-3'-dimethylsulfamoylacetophenone required for this is described in the German Offenlegungsschrift No. 2,926,771.

EXAMPLE 7

4-(2-Chloro-5-dimethylsulfamoylphenyl)-2-(4-hydroxyphenylimino)-3-methyl-4-thiazoline (a) is obtained analogously to the procedure given in Example 2(a) from 4-(2-chloro-5-dimethylsulfamoylphenyl)-2-(4-hydroxyphenylimino)-3-methyl-4-thiazoline hydrobromide (Example 60) but, instead of triethylamine, a cold 20% strength methanolic ammonia solution is used to basify, working-up is as in Example 2(a)

and the dried crystalline crude product is recrystallized from ethanol, m.p. 220°–22° C.

(b) is obtained analogously to the procedure given in Example 2(c) from 2'-chloro-5'-dimethyl-sulfamoylacetophenone-2-thiol (m.p. 100°–115° C.) and N-methyl-N'-(4-hydroxyphenyl)-chloroformamidine hydrochloride. M.p. 221°–224° C. (from ethanol).

EXAMPLE 8

4-(4-Chloro-3-dimethylsulfamoylphenyl)-2-(4-acetoxyphenylimino)-3-methyl-4-thiazoline 2.1 g (5 mmoles) of 4-(4-chloro-3-dimethylsulfamoylphenyl)-2-(4-hydroxyphenylimino)-3-methyl-4-thiazoline (Example 2) are suspended in 25 ml of acetic anhydride and the yellow solution which results on warming, is stirred for 1 hour at 120° C. After distilling off the acetic anhydride in vacuo, the solid residue is recrystallized from isopropanol. Colorless crystals of m.p. 173°–174° C.

EXAMPLE 9

4-(4-Chloro-3-dimethylsulfamoylphenyl)-2-(4-propionyloxyphenylimino)-3-methyl-4-thiazoline 2 g (4.7 mmoles) of 4-(4-chloro-3-dimethylsulfamoylphenyl)-2-(4-hydroxyphenylimino)-3-methyl-4-thiazoline is suspended in 40 ml of dry chloroform. 0.4 g (4.7 mmoles) of propionyl chloride (dissolved in 10 ml of chloroform) and 1.4 g (18 mmoles) of pyridine are added in that order. A slightly exothermic reaction produces, temporarily, a solution from which a yellow solid precipitates. After stirring for 3 hours at room temperature, a further 0.4 ml of propionyl chloride is added. The resulting yellow solution is allowed to stand for 3 days at room temperature and then evaporated to dryness in vacuo, the residue is distributed between water and ethyl acetate, the organic phase is dried and evaporated and the residue is recrystallized from isopropanol. Colorless crystals of m.p. 155°–159° C.

EXAMPLE 10

4-(3-Chloro-5-dimethylsulfamoylphenyl)-2-(4-hydroxyphenylimino)-3-methyl-4-thiazoline is obtained from 4-(3-chloro-5-dimethylsulfamoylphenyl)-2-(4-hydroxyphenylimino)-3-methyl-4-thiazoline hydrobromide (m.p. 285° C. (decomp.)), prepared analogously to Example 1(a) or 1(b) by reaction with triethylamine in ethanol analogously to Example 2(a), colorless crystals, of m.p. 155°–158° C.

The 2-bromo-3'-chloro-5'-dimethylsulfamoylacetophenone, necessary for the preparation, is described in German Offenlegungsschrift No. 2,926,771.

EXAMPLE 11

4-(4-Chloro-3-dimethylsulfamoylphenyl)-2-(4-hydroxyphenylimino)-3-methyl-thiazolidin-4-ol hydrobromide 6.8 g (0.02 mole) of 2-bromo-4'-chloro-3'-dimethylsulfamoylacetophenone are dissolved in 60 ml of acetone or 150 ml of ethanol or 50 ml of ethyl acetate and, after addition of a solution of 3.7 g (0.022 mole) of 1-(4-hydroxyphenyl)-3-methyl-thiourea in 60 ml of acetone or 50 ml of ethanol or 100 ml of ethyl acetate, the solution is stirred at room temperature for 1 to 4 hours, the crystals are filtered off and, after washing with a little acetone and ether, dried in a cool stream of air or in vacuo over paraffin shavings. Colorless crystals, m.p. 255°–264° C. with decomposition, by slow heating; m.p. 178°–180° C., by rapid heating.

The procedures (a) to (e), described in the practical Examples 1–10, are suitable for the preparation of the compounds listed in Table 4 (practical Examples 12 to 104).

By a method analogous to that in practical Example 11 are obtained the precursors or intermediates 105–149, described in Table 5, whose melting points or decomposition temperatures are very dependent on the rate of heating, due to the often unnoticed elimination of water on heating and the consequent possible transition into compounds of the general structure I.

TABLE 4

(Explanations of Table 3)

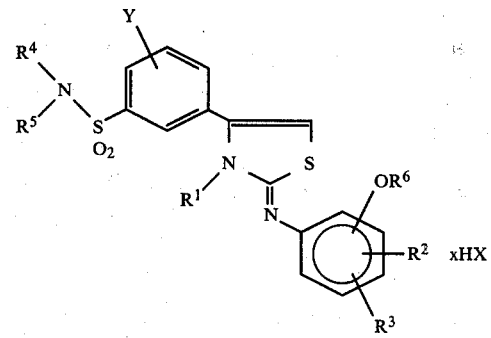

| Example No. | Y | R¹ | R² | R³ | R⁴ | R⁵ | OR⁶ | HX | M.p. (°C.) |
|---|---|---|---|---|---|---|---|---|---|
| 12 | 4-Cl | Me | H | H | Me | H | 4-OH | HBr | 272 Decomp. |
| 13 | 4-Cl | Me | H | H | H | H | 4-OH | HBr | 274 Decomp. |
| 14 | 4-Cl | Me | H | H | Me | H | 4-OH | — | 128–130 |
| 15 | 6-Cl | Me | H | 5-Me | Me | Me | 2-OH | — | 185–189 |
| 16 | 4-Cl | Me | H | 5-Me | H | H | 2-OH | HBr | 278–282 Decomp. |
| 17 | 6-Cl | Me | H | 5-Me | Me | Me | 2-OH | HBr | 254–256 Decomp. |
| 18 | 4-Cl | Me | H | 5-Me | Me | Me | 2-OH | — | 188–192 |
| 19 | 4-Cl | Me | H | 5-Me | Me | Me | 2-OH | HBr | 255–259 Decomp. |

TABLE 4-continued
(Explanations of Table 3)

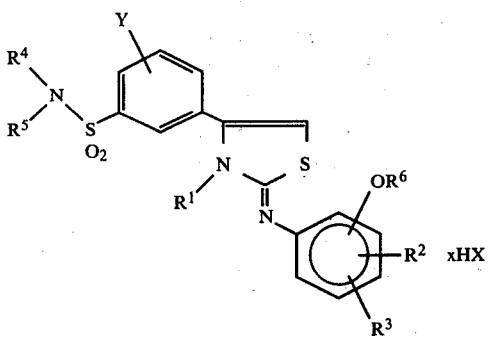

| Example No. | Y | R¹ | R² | R³ | R⁴ | R⁵ | OR⁶ | HX | M.p. (°C.) |
|---|---|---|---|---|---|---|---|---|---|
| 20 | 4-Cl | Me | H | H | n-Bu | H | 4-OH | — | 122–125 |
| 21 | 4-Cl | Me | H | H | n-Bu | H | 4-OH | HBr | 285 Decomp. |
| 22 | 4-Cl | Me | H | H | n-Pr | H | 4-OH | — | 127–131 Decomp. |
| 23 | 4-Cl | Me | H | H | n-Pr | H | 4-OH | — | 298–300 Decomp. |
| 24 | 4-Cl | Me | H | 2-Me | H | H | 5-OH | — | 188–191 |
| 25 | 4-Cl | Me | H | 2-Me | H | H | 5-OH | HBr | 282 Decomp. |
| 26 | 4-Cl | Me | H | H | Et | H | 4-OH | — | 126–129 Decomp. |
| 27 | 4-Cl | Me | H | H | Et | H | 4-OH | HBr | 277–280 Decomp. |
| 28 | 4-Cl | Et | H | H | Et | Et | 4-OH | — | 166–170 |
| 29 | 4-Cl | Et | H | H | Et | Et | 4-OH | HBr | 265 Decomp. |
| 30 | 4-Cl | Et | H | H | Me | Me | 4-OH | — | 230–250 |
| 31 | 4-Cl | Et | H | H | Me | Me | 4-OH | HBr | 130–160 Decomp. |
| 32 | 4-Cl | Me | H | H | H | H | 3-OH | — | 206–208 |
| 33 | 4-Cl | Me | H | H | H | H | 3-OH | HBr | 277 Decomp. |
| 34 | 4-Cl | Me | 3-Cl | 5-Cl | H | H | 4-OH | — | 235–236 Decomp. |
| 35 | 4-Cl | Me | 3-Cl | 5-Cl | H | H | 4-OH | HBr | 291 Decomp. |
| 36 | 4-Cl | Me | H | H | H | 2-Bu | 4-OH | — | 125 Decomp. |
| 37 | 4-Cl | Me | H | H | H | 2-Bu | 4-OH | HBr | 276 Decomp. |
| 38 | 4-Cl | Me | H | H | Et | Et | 4-OH | — | 235–237 |
| 39 | 4-Cl | Me | H | H | Et | Et | 4-OH | HBr | 273 Decomp. |
| 40 | 4-Cl | Me | H | 2-Cl | Me | Me | 4-OH | — | 197–200 |
| 41 | 4-Cl | Me | H | 2-Cl | Me | Me | 4-OH | HBr | 264 Decomp. |
| 42 | 6-Cl | Me | H | 2-Cl | Me | Me | 4-OH | — | 230–235 |
| 43 | 6-Cl | Me | H | 2-Cl | Me | Me | 4-OH | HBr | 264 Decomp. |
| 44 | 6-Cl | Me | H | 2-Me | Me | Me | 5-OH | — | 246–248 |
| 45 | 6-Cl | Me | H | 2-Me | Me | Me | 5-OH | HBr | 265–268 Decomp. |
| 46 | 4-Cl | Me | H | 2-Cl | Et | Et | 4-OH | — | 220–223 |
| 47 | 4-Cl | Me | H | 2-Cl | Et | Et | 4-OH | HBr | 267 Decomp. |
| 48 | 4-Cl | Me | H | 2-Cl | H | Me | 4-OH | — | 112–115 |
| 49 | 4-Cl | Me | H | 2-Cl | H | Me | 4-OH | HBr | 279–281 Decomp. |
| 50 | 5-Cl | Me | H | 2-Cl | Me | Me | 4-OH | — | 133–140 Decomp. |
| 51 | 5-Cl | Me | H | 2-Cl | Me | Me | 4-OH | HBr | 247 Decomp. |
| 52 | 4-Cl | Me | H | H | H | H | 2-OH | — | 206–208 |
| 53 | 4-Cl | Me | H | H | H | H | 2-OH | HBr | 268–269 Decomp. |
| 54 | 4-Br | Me | H | H | H | H | 4-OH | — | 209–211 |
| 55 | 4-Br | Me | H | H | H | H | 4-OH | HBr | 254 Decomp. |
| 56 | 4-Cl | Me | H | 2-Me | Me | Me | 5-OH | — | 169–172 Decomp. |
| 57 | 4-Cl | Me | H | 2-Me | Me | Me | 5-OH | HBr | 270–272 Decomp. |
| 58 | 4-Cl | Me | H | 3-Me | Me | Me | 4-OH | — | 208–211 |
| 59 | 4-Cl | Me | H | 3-Me | Me | Me | 4-OH | HBr | 267–270 Decomp. |
| 60 | 6-Cl | Me | H | H | Me | Me | 4-OH | HBr | 302–305 Decomp. |
| 61 | 6-Cl | Me | H | H | Me | Me | 2-OH | — | 194–195 |
| 62 | 6-Cl | Me | H | H | Me | Me | 2-OH | HBr | 237 Decomp. |
| 63 | 4-Cl | Me | H | H | Me | Me | 2-OH | — | 203–204 |
| 64 | 4-Cl | Me | H | H | Me | Me | 2-OH | HBr | 252 Decomp. |
| 65 | 4-Cl | Me | H | 2-Cl | H | H | 4-OH | — | 252–255 Decomp. |
| 66 | 4-Cl | Me | H | 2-Cl | H | H | 4-OH | HBr | 270 Decomp. |
| 67 | 4-Cl | Me | H | H | Me | Me | 3-OH | (xH₂O) | 129 Decomp. |
| 68 | 4-Cl | Me | H | H | Me | Me | 3-OH | HBr | 267 Decomp. |
| 69 | 5-Cl | Me | H | H | Me | Me | 2-OH | — | 191–192 |
| 70 | 5-Cl | Me | H | H | Me | Me | 2-OH | HBr | 258 Decomp. |
| 71 | 5-Cl | Me | H | 2-Me | Me | Me | 5-OH | HBr | 247–250 Decomp. |
| 72 | 5-Cl | Et | H | H | Me | Me | 4-OH | HBr | 223–230 Decomp. |
| 73 | 6-Cl | Et | H | H | Me | Me | 4-OH | HBr | 267–270 Decomp. |
| 74 | 4-Cl | Me | H | H | Me | Me | 4-OH | TsOH | 246–248 Decomp. |
| 75 | 4-Cl | Me | H | H | Me | Me | 4-OH | MsOH | 270–272 |
| 76 | 4-Br | Me | H | H | H | H | 4-OH | — | 209–211 |
| 77 | 4-Br | Me | H | H | H | H | 4-OH | HBr | 254 Decomp. |
| 78 | 4-Cl | Me | 3-Cl | 5-Cl | Me | Me | 4-OH | HBr | 330 |
| 79 | 4-Cl | Me | H | 3-OMe | Me | Me | 4-OH | (xH₂O) | 163–166 |
| 80 | 4-Cl | Me | H | 3-OMe | Me | Me | 4-OH | HBr | 255–257 Decomp. |

TABLE 4-continued (Explanations of Table 3)

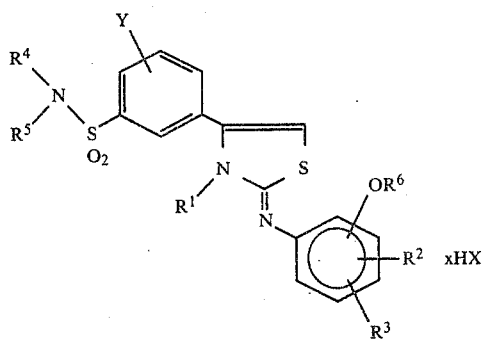

| Example No. | Y | $R^1$ | $R^2$ | $R^3$ | $R^4$ | $R^5$ | $OR^6$ | HX | M.p. (°C.) |
|---|---|---|---|---|---|---|---|---|---|
| 81 | 4-Cl | Me | H | 4-i-Pr | Me | Me | 3-OH | — | 108–115 Decomp. |
| 82 | 4-Cl | Me | H | 4-i-Pr | Me | Me | 3-OH | HBr | 269 Decomp. |
| 83 | 5-Me | Me | H | H | Me | Me | 4-OH | HBr | 310–316 Decomp. |
| 84 | 6-Me | Me | H | H | Me | Me | 4-OH | — | 127–133 |
| 85 | 6-Me | Me | H | H | Me | Me | 4-OH | HBr | 293–296 Decomp. |
| 86 | 4-Cl | Me | H | H | H | H | 4-OH | HCl | 270–272 Decomp. |
| 87 | 4-Me | Me | H | H | Me | Me | 4-OH | — | 210 Decomp. |
| 88 | 4-Cl | Et | H | H | H | H | 4-OH | HBr | 165–168 Decomp. |
| 89 | 4-Cl | Me | H | 3-Me | H | H | 4-OH | HBr | 258–260 |
| 90 | 4-Cl | Me | H | 3-Me | H | H | 4-OH | (xEtOH) | 134–137 Decomp. |
| 91 | 4-Cl | Me | H | 3-Cl | H | H | 4-OH | — | 210–225 Decomp. |
| 92 | 4-Cl | Me | H | 3-Cl | H | H | 4-OH | HBr | 293 Decomp. |
| 93 | 4-Cl | Me | 3-Cl | 4-Me | H | H | 2-OH | HBr | 273 Decomp. |
| 94 | 4-Cl | Me | 3-Cl | 4-Me | H | H | 2-OH | — | 188–190 |
| 95 | 4-Cl | Me | 3-t-Bu | 5-t-Bu | H | H | 4-OH | — | 239–240 |
| 96 | 4-Cl | Me | 3-t-Bu | 5-t-Bu | Me | Me | 4-OH | — | 228–229 |
| 97 | 4-Cl | Me | 3-t-Bu | 5-t-Bu | H | H | 4-OH | HBr | 207 Decomp. |
| 98 | 4-Cl | Me | 3-t-Bu | 5-t-Bu | Me | Me | 4-OH | HBr | 238 Decomp. |
| 99 | 4-Cl | Me | 3-Me | 5-Me | Me | Me | 4-OH | — | 188–189 |
| 100 | 4-Cl | Me | 3-Me | 5-Me | Me | Me | 4-OH | HBr | 266 Decomp. |
| 101 | 4-Cl | Me | 3-Me | 5-Me | H | H | 4-OH | HBr | 250 Decomp. |
| 102 | 4-Cl | Me | 3-Me | 5-Me | H | H | 4-OH | — | 233–234 |
| 103 | 4-Cl | Me | H | H | —(CH$_2$)$_4$— | | 4-OH | HBr | 276 Decomp. |
| 104 | 4-Cl | Me | H | H | —(CH$_2$)$_4$— | | 4-OH | — | 197–198 |

TABLE 5

(Explanation cf. Table 3)

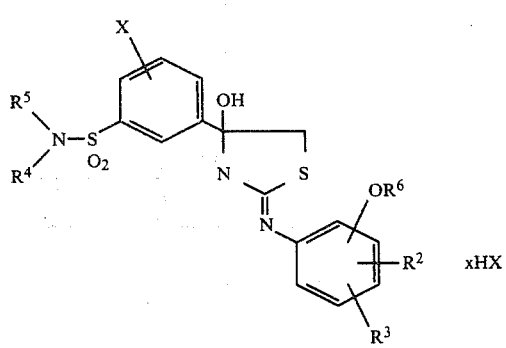

| Example No. | Y | $R^1$ | $R^2$ | $R^3$ | $R^4$ | $R^5$ | $OR^6$ | HX | M.p. (°C.) |
|---|---|---|---|---|---|---|---|---|---|
| 105 | 4-Cl | Me | 3-Cl | 5-Cl | H | H | 4-OH | HBr | 286 Decomp. |
| 106 | 4-Cl | Me | H | 3-Cl | H | H | 4-OH | HBr | 199 Decomp. |
| 107 | 4-Cl | Me | H | H | H | H | 3-OH | HBr | 152 Decomp. |
| 108 | 4-Cl | Me | H | H | H | 2-Bu | 4-OH | HBr | 277 Decomp. |
| 109 | 4-Cl | Me | H | H | Et | Et | 4-OH | HBr | 276 Decomp. |
| 110 | 4-Cl | Me | 3-Cl | 5-Cl | Me | Me | 4-OH | HBr | 264 Decomp. |
| 111 | 4-Cl | Me | H | H | Me | Me | 3-OH | HBr | 263 Decomp. |
| 112 | 4-Cl | Me | 4-Me | 5-Cl | H | H | 2-OH | HBr | 276 Decomp. |
| 113 | 4-Cl | Me | H | H | H | H | 2-OH | HBr | 182 Decomp. |
| 114 | 5-Cl | Me | H | H | Me | Me | 4-OH | HBr | 282 Decomp. |
| 115 | 5-Cl | Me | H | H | Me | Me | 2-OH | HBr | 248 Decomp. |

TABLE 5-continued (Explanation cf. Table 3)

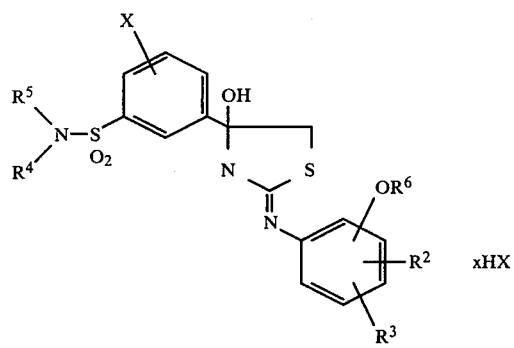

| Example No. | Y | R¹ | R² | R³ | R⁴ | R⁵ | OR⁶ | HX | M.p. (° C.) |
|---|---|---|---|---|---|---|---|---|---|
| 116 | 6-Cl | Me | H | H | Me | Me | 2-OH | HBr | 198 Decomp. |
| 117 | 5-Cl | Me | H | H | Me | Me | 2-OH | HBr | 261 Decomp. |
| 118 | 4-Cl | Me | H | H | H | H | 4-OH | HBr | 170 Decomp. |
| 119 | 4-Cl | Me | H | H | Me | H | 4-OH | HBr | 155/267 Decomp. |
| 120 | 4-Cl | Me | H | H | Me | Me | 4-OH | — | 121 Decomp. |
| 121 | 4-Cl | Me | H | H | H | Me | 4-OH | — | 142 Decomp. |
| 122 | 4-Cl | Me | H | H | H | H | 4-OH | — | 174 Decomp. |
| 123 | 4-Cl | Me | H | 5-Me | H | H | 2-OH | HBr | 185/220 Decomp. |
| 124 | 4-Cl | Et | H | H | H | H | 4-OH | HBr | 175 Decomp. |
| 125 | 4-Cl | Me | 4-Me | 5-Me | H | H | 2-OH | HBr | 220-5 Decomp. |
| 126 | 6-Cl | Me | 5-Me | H | Me | Me | 2-OH | HBr | 255 Decomp. |
| 127 | 4-Cl | Me | H | 3-Me | H | H | 4-OH | HBr | 188-92 Decomp. |
| 128 | 4-Cl | Me | H | 2-Cl | H | H | 4-OH | HBr | 156 Decomp. |
| 129 | 4-Cl | Me | H | 5-Me | Me | Me | 4-OH | HBr | 260 Decomp. |
| 130 | 4-Cl | Me | H | H | n-Bu | H | 4-OH | HBr | 187-90 Decomp. |
| 131 | 4-Cl | Me | H | H | Et | H | 4-OH | HBr | 175-178 Decomp. |
| 132 | 4-Cl | Me | H | H | n-Pr | H | 4-OH | HBr | 183-5 Decomp. |
| 133 | 4-Cl | Et | H | H | Me | Me | 4-OH | HBr | 190 Decomp. |
| 134 | 4-Cl | Me | 2-Me | H | H | H | 5-OH | HBr | 189-99 Decomp. |
| 135 | 4-Cl | Et | H | H | Et | Et | 4-OH | HBr | 263-5 Decomp. |
| 136 | 4-Cl | Me | 2-Cl | H | Me | Me | 4-OH | HBr | 276 Decomp. |
| 137 | 6-Cl | Me | 2-Cl | H | Me | Me | 4-OH | HBr | 210-4 Decomp. |
| 138 | 6-Cl | Me | 2-Me | H | Me | Me | 5-OH | HBr | 198-201 Decomp. |
| 139 | 4-Cl | Me | 2-Me | H | Me | Me | 5-OH | HBr | 266 Decomp. |
| 140 | 4-Cl | Me | 2-Cl | H | Et | Et | 4-OH | HBr | 266 Decomp. |
| 141 | 4-Cl | Me | 2-Cl | H | Me | H | 4-OH | HBr | 280 Decomp. |
| 142 | 5-Cl | Me | 2-Cl | H | Me | Me | 4-OH | HBr | 218-21 Decomp. |
| 143 | 4-Cl | Me | 2-Me | H | Me | Me | 4-OH | HBr | 268 Decomp. |
| 144 | 6-Cl | Me | H | H | Me | Me | 4-OH | HBr | 298 Decomp. |
| 145 | 5-Cl | Et | H | H | Me | Me | 4-OH | HBr | 130 Decomp. |
| 146 | 4-Br | Me | H | H | H | H | 4-OH | HBr | 168 Decomp. |
| 147 | 4-Me | Me | H | H | Me | Me | 4-OH | HBr | 220-40 Decomp. |
| 148 | 6-Me | Me | H | H | Me | Me | 4-OH | HBr | 180 Decomp. |
| 149 | 5-Me | Me | H | H | Me | Me | 4-OH | HBr | 310 Decomp. |

TABLE 6 shows some of the thioureas III, prepared by methods known from the literature (cf. page 7)

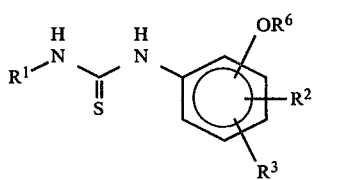 (III)

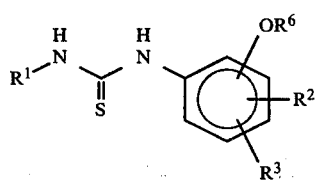 (III)

(Abbreviations as in Table 3)

| R¹ | R² | R³ | OR⁶ | M.p. (°C.) | R¹ | R² | R³ | OR⁶ | M.p. (°C.) |
|---|---|---|---|---|---|---|---|---|---|
| Me | H | H | 4-OH | 195-196 | Me | H | H | 3-OH | 165-167 |
| Me | 5-Me | H | 2-OH | 176-179 | Me | H | H | 2-OH | 123-126 |
| Et | H | H | 4-OH | 152-155 | Me | 3-Cl | H | 4-OH | 216-218 |
| Me | 3-Me | H | 4-OH | 233-236 | Me | 3-Cl | 5-Cl | 4-OH | 204-206 |
| Me | 2-Cl | H | 4-OH | 164-167 | Me | 3-t-Bu | 5-t-Bu | 4-OH | 198-200 |
| Me | 4-Me | 5-Me | 2-OH | 158-162 | Me | 3-Me | 5-Me | 4-OH | 200-201 |
| Me | 2-Me | H | 5-OH | 202-205 | Me | 3-OMe | H | 4-OH | 193-195 |

TABLE 6-continued shows some of the thioureas III, prepared by methods
known from the literature (cf. page 7)

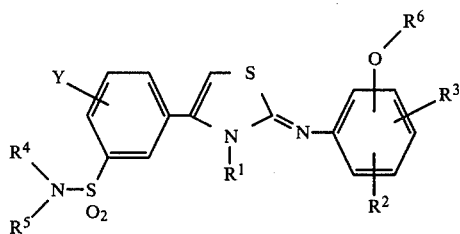

(III)

(Abbreviations as in Table 3)

| $R^1$ | $R^2$ | $R^3$ | $OR^6$ | M.p. (°C.) |
|---|---|---|---|---|
| Me | 4-i-Pr | H | 3-OH | 145–147 |

We claim:

1. A thiazoline derivative of the formula

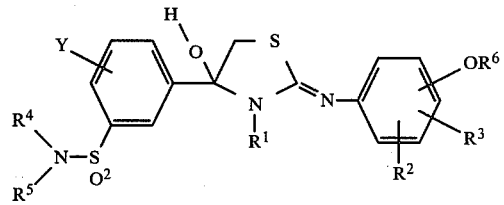

or a physiologically tolerated salt thereof, in which $R^1$ is alkyl with 1 to 3 C atoms, $R^2$ and $R^3$ are hydrogen, halogen, alkyl or alkoxy with 1 to 4 C atoms, and are identical or different, $R^4$ and $R^5$ are hydrogen or alkyl with 1 to 4 C atoms, and are identical or different or together with the N atom form a saturated ring with up to 6 ring members, $R^6$ is hydrogen or an aliphatic acyl group with 1 to 4 C atoms and Y is hydrogen, halogen, or methyl.

2. The thiazoline derivative defined in claim 1, wherein $R^1$ is methyl or ethyl, $R^2$ is hydrogen or chlorine, $R^3$ is hydrogen or chlorine or methyl, $R^4$ is hydrogen or methyl or ethyl, $R^5$ is hydrogen or methyl, $R^6$ is hydrogen or —CO—CH$_3$ or —COC$_2$H$_5$, Y is chlorine, bromine or methyl in the 4-,5- or 6-position to the thiazoline ring, the sulfamoyl radical being fixed in the 3-position.

3. The thiazoline derivative defined in claim 1, in which $R^1$ is methyl, $R^2$ and $R^3$ are hydrogen, $R^4$ is hydrogen or methyl, $R^5$ is hydrogen or methyl, $R^6$ is hydrogen, the OH group being in the 4-position to the imino group and Y is chlorine in the 4-position to the thiazoline.

4. 4-(4-Chloro-3-sulfamoylphenyl)-2-(4hydroxyphenylimino)-3-methyl-4-thiazoline as claimed in claim 1 as well as its pharmacologically tolerated acid addition salts.

5. 4-(4-Chloro-3-methylsulfamoylphenyl)-2-(4-hydroxyphenylimino)-3-methyl-4-thiazoline as claimed in claim 1 as well as its pharmacologically tolerated acid addition salts.

6. 4-(4-Chloro-3-dimethylsulfamoylphenyl)-2-(4-hydroxyphenylimino)-3-methyl-4-thiazoline as claimed in claim 1 as well as its pharmacologically tolerated acid addition salts.

7. A process for the treatment of serum lipoprotein disorders which comprises administering a pharmaceutically effective amount of a compound as defined in claim 1 and a carrier therefor.

8. A pharmaceutical composition for the treatment of serum lipoprotein disorders comprising a pharmaceutically effective amount of a compound as defined in claim 1 and a carrier therefor.

9. A compound of the formula wherein $R^1$ and $R^6$ and Y have the meanings given for formula I, or its salts.

* * * * *